United States Patent
Pfeifer et al.

(10) Patent No.: US 10,342,745 B2
(45) Date of Patent: Jul. 9, 2019

(54) METHACRYLAMIDE COMPOUNDS

(71) Applicants: Carmem S. Pfeifer, Beaverton, OR (US); Jack L. Ferracane, Beaverton, OR (US); Wilbes Mbiya, Portland, OR (US)

(72) Inventors: Carmem S. Pfeifer, Beaverton, OR (US); Jack L. Ferracane, Beaverton, OR (US); Wilbes Mbiya, Portland, OR (US)

( * ) Notice: Subject to any disclaimer, the term of this patent is extended or adjusted under 35 U.S.C. 154(b) by 0 days.

(21) Appl. No.: 15/154,699

(22) Filed: May 13, 2016

(65) Prior Publication Data

US 2016/0331647 A1    Nov. 17, 2016

Related U.S. Application Data

(60) Provisional application No. 62/161,043, filed on May 13, 2015.

(51) Int. Cl.
*C07D 237/00* (2006.01)
*A61K 6/083* (2006.01)
*A61K 6/09* (2006.01)
*C07D 403/12* (2006.01)
*C07D 401/12* (2006.01)

(52) U.S. Cl.
CPC ............... *A61K 6/083* (2013.01); *A61K 6/09* (2013.01); *C07D 401/12* (2013.01); *C07D 403/12* (2013.01)

(58) Field of Classification Search
CPC .................... C07D 401/12; C07D 403/12
See application file for complete search history.

(56) References Cited

U.S. PATENT DOCUMENTS

| | | |
|---|---|---|
| 2003/0055124 A1 | 3/2003 | Klee |
| 2010/0041790 A1 | 2/2010 | Moszner et al. |
| 2010/0249276 A1 | 9/2010 | Dersham |
| 2013/0199724 A1 | 8/2013 | Dershem |

OTHER PUBLICATIONS

PCT/US2016/032481 International Search Report dated Aug. 26, 2016.

*Primary Examiner* — Michael L Leonard (57) ABSTRACT

New methacrylate compounds are disclosed as well as compositions comprising the methacrylate compounds and thiourethane oligomers. These compositions can be used in, for example, dental composites.

14 Claims, 2 Drawing Sheets

METHACRYLAMIDE COMPOUNDS

ACKNOWLEDGEMENT OF GOVERNMENT SUPPORT

This invention was made with the support of the United States government under the terms of grant number U01 DE02756, awarded by the National Institutes of Health. The United States government has certain rights to this invention.

FIELD

Generally, the field is methacrylamides. More specifically, the field is methacrylamide monomers that can be used, for example, in combination with thiourethane oligomers.

BACKGROUND

The service life of dental composite restorations averages 7 years. The main causes for replacement are secondary caries and fracture. Some controlled clinical studies, for mostly conservative composite restorations, show survivals of 10-20 years. But data from cross-sectional and other controlled studies prove that current formulations are not adequately stable. Material degradation over time in the mouth, coupled with variations in microflora and caries risk in certain patients, greatly contributes to reduced service life.

While most of the improvements in composites have come from altering the filler technology, recently new monomers have been developed to decrease polymerization shrinkage and its associated stress. However, most still rely on resin matrices with methacrylate chemistry. The main disadvantage of methacrylates is the relatively low resistance to degradation by hydrolysis and enzymatic attack by esterases, leading to breakdown of the restorative material and the composite/tooth interface. Therefore, there is an urgent need to develop new composites based on more stable compounds, while at the same time maintaining or exceeding the mechanical properties and shrinkage/stress behavior of current commercial materials.

Methacrylate monomers have been used as the main constituents in the resin matrix in composite materials for over 50 years. Their relative success derives from excellent aesthetic properties, convenient and fast cure on command, rigidity similar to dentin, and mechanical stability. Despite these aspects, there are significant negative attributes that limit their longevity in the oral cavity, such as high shrinkage and accompanying stress, lower than desirable fracture toughness, relatively low degree of conversion (DC), and high rate of degradation by hydrolysis and enzymatic attack of the resin matrix and the composite/tooth interfacial bond. The goal of this proposal is to develop novel resin systems that will maintain or improve upon the beneficial assets while addressing the shortcomings of methacrylates.

Many available monomers, such as epoxies, vinyl ethers, allyl ethers, maleimides or (meth)acrylamides, may offer greater resistance to hydrolytic/enzymatic attack than methacrylates.

SUMMARY

Described herein are improved polymers for dental composites based on biocompatible tertiary methacrylamides with the following advantages: First, they allow initiation and fast/effective propagation to high conversions through a free-radical mechanism, while maintaining the feature of on command polymerization initiated by visible light. This is preferable to other curing mechanisms, such as cationic/anionic, which are sensitive to environmental moisture, as well as to filler particle surface charge. In addition, this chemistry ensures that in situ curing with current light activated polymerization schemes already familiar to dentists can be used, enhancing their acceptance by the profession. Second, their glass transition temperature (Tg) is similar to that of methacrylates. Third, (meth)acrylamides have the best hydrolytic stability of the monomers cited. Primary and secondary (meth)acrylamides usually have relatively high melting temperatures, and also are prone to degradation by amylases. This is not the case for the compounds disclosed herein, because the N—H bond typically required in the protease-based hydrolysis is not present. Moreover, N,N-dialkyl amide bonds are much bulkier than the amide bonds in proteins and hinder the fit in the catalytic center of a protease for hydrolysis. Finally, a variety of backbone structures can be designed from this platform, to include flexible/stiff extenders and to control the magnitude of secondary intermolecular interactions (i.e. hydrogen bonding and pi-stacking), which in turn control mechanical properties.

Described are compounds with the structure:

wherein X is a 5- or 6-membered heterocycloalkyl, wherein n is an integer selected from 0, 1, and 2, and wherein R is selected from alkyl, substituted alkyl, aryl, substituted aryl, or dicycloalkyl. In further examples, R is selected from:

Also described are the disclosed compounds in a composition further comprising thiourethane oligomers as well as dental composites comprising the compositions.

DETAILED DESCRIPTION

Alkyl: a branched or unbranched saturated hydrocarbon group, such as, without limitation, methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like. A lower alkyl group is a saturated branched or unbranched hydrocarbon having from 1 to 6 carbon atoms ($C_{1-6}$alkyl). The term alkyl also encompasses cycloalkyls. Alkyl also encompasses substituted alkyls which are alkyl groups wherein one or more hydrogen atoms are replaced with a substituent such as, without limitation, alkyl, alkynyl, alkenyl, aryl, halide, nitro, amino, ester, ether, ketone, aldehyde, hydroxyl, carboxyl, cyano, amido, haloalkyl, haloalkoxy, or alkoxy. The term alkyl also encompasses heteroalkyls. A heteroalkyl contains at least one heteroatom such as nitrogen, oxygen, sulfur, or phosphorus replacing one or more of the carbons. Substituted heteroalkyls are also encompassed by the term alkyl. A dicycloalkyl is a branched or unbranched alkyl substituted with two substituted or unsubstituted cycloalkyls.

Aryl: any carbon-based aromatic group including, but not limited to, benzene, naphthalene, and phenyl. The term aryl also contemplates substituted aryls in which one or more of the hydrogens is substituted with one or more groups including but not limited to alkyl, alkynyl, alkenyl, aryl, halide, nitro, amino, ester, ether, ketone, aldehyde, hydroxy, carboxylic acid, cyano, amido, haloalkyl, haloalkoxy, or alkoxy. The term aryl also contemplates heteroaryls in which one or more of the carbons is replaced by a heteroatom. Examples of heteroatoms include, but are not limited to, nitrogen, oxygen, sulfur, and phosphorous. Substituted heteroaryls are also encompassed by the term aryl.

Cycloalkyl: a non-aromatic carbon-based ring composed of at least three carbon atoms. Examples of cycloalkyl groups include, but are not limited to, cyclopropyl, cyclobutyl, cyclopentyl, and cyclohexyl. Cycloalkyls also encompass substituted cycloalkyls and heterocycloalkyls where at least one of the carbon atoms is replaced with a heteroatom such as nitrogen, sulfur or phosphorus. A heterocycloalkyl wherein one or more of the carbons is replaced with nitrogen is also termed a cycloalkylamino herein. The term also encompasses substituted heterocycloalkyls.

Methacrylamides are well known for their hydrolytic stability and, specifically for tertiary methacrylamides, resistance to protease degradation. Synthetic pathways have been designed to produce novel methacrylamides that can be screened for their mechanical and chemical suitability as dental monomers by flexure testing (ISO4049), polymerization kinetics (FTIR), and enzymatic and hydrolytic resistance by comparison with known controls and established targets. Such new methacrylamide compounds can be further tested for polymerization shrinkage, polymerization stress, depth of cure, water sorption/solubility, demonstration of reduced degradation in water/enzymes in low pH, and adequate resistance to cyclic fatigue, to determine that the disclosed resins have improved properties relative to current methacrylate resins.

Using the disclosed methacrylamide monomers, microhybrid composites can be formulated with at least 75% (by weight) silane-treated filler, and tested according to the same scheme as the neat polymers. Subsequently, an intraoral physiologic simulator composed of a biofilm forming/mechanical fatiguing device can be used to study the resistance of the novel composite restoratives placed in defined cavities to surface and tooth-restorative interfacial failure compared to current commercial methacrylate-based composites during six years of clinical simulation.

The disclosed methacrylamide monomers can be added to thiourethane oligomers thereby providing the resulting composites with systematically enhanced fracture toughness based on the structure and rigidity of the backbone of the isocyanate or thiol precursor molecules used. The addition of thiourethane oligomers also can also result in less shrinkage of the resin (proportionally to the concentration of oligomer), such as less than 4%.

The disclosed methacrylamide monomers can be used in conjunction with an adhesive system in order for it to interact with the tooth. The disclosed tertiary methacrylamide monomers can be used in low-viscosity formulations (by the addition of solvents and hydrophilic, small molecular weight monomers) in conjunction with an etch-and-rinse protocol. Bond strength can be assessed after restoration and after 6 months of storage in physiological conditions. The activity of dentin enzymes can be evaluated through zymography. Results can be compared with those of other methacrylate systems.

Synthesis:

Scheme 1

Scheme 1 is a route to produce more reactive methacrylamides. 3-methylenepiperidin-2-one is reacted with 1,2-di (1l³-oxiran-1-yl)ethane in water for 5-24 hours at room temperature to yield compound 3b.

Scheme 2 is a synthetic route to produce methacrylamides tested as described herein.

In Step A of Scheme 2, Methacryloyl chloride (2.1 mol) in dichloromethane (8 mL) was added dropwise to a stirred solution of 4-hydroxypiperidine (2.0 mols) and triethylamine (TEA, 2.1 mols) which was the acid scavenger in dichloromethane (25 mL) at 0° C. under an inert atmosphere (Nitrogen gas). After the addition was complete, the reaction mixture was stirred at 0° C. for a further 2 hrs and 0.05 mols of 4-dimethylaminopyridine (DMAP) a catalyst was added. The reaction was allowed to proceed at room temperature for 22 hrs. After that, the 2-ethylamino-ethanol monohydrochloride was extracted with 10% (w/v) sodium hydroxide in water and the organic portion was extracted with dichloromethane (3×40 mL) using a separator funnel. The organic portion was dried using sodium sulfate and then evaporated under reduce pressure to give the crude product as yellow oil. The residue was purified by a silica gel column using ethyl acetate:hexane:methanol ratio (8:1:1). The final product, which was a pale yellow liquid (yield 78-86%) was characterized using $^1$H NMR, FT-IR and HRMS.

In Step B the methacrylamide (2.1 mols) made in step A was mixed with 1.0 mol of diisocyanate (BDI, DESM or HDDI) in 25 mL of tetrahydrofuran (THF) and a drop of the catalyst dibutyl tin dilaurate (DTD) was added. The reaction was heated to 50° C. under reflux while monitoring the disappearance of the isocyanate peak at ~2270 cm$^{-1}$ using IR for 18 to 24 hrs. The removal of the solvent using rotary vapor gave a clear viscous liquid (yield <96%) which was characterized using $^1$H NMR, FT-IR and HRMS.

The compounds described herein can be combined with thiourethane oligomers. As described in PCT/US15/21016 (incorporated by reference herein), isocyanates and thiols can be reacted with one another to form thiourethane networks. Such networks result in improved toughness, a high refractive index, and optical clarity. For example, a Flory-Stockmeyer equation can be used to select starting amounts of isocyanates and thiols to result in pendant isocyanate or pendant thiol groups which can be in turn be functionalized with the methacrylamide compounds described herein.

For example, a thiol terminated thiourethane oligomer can be produced when an excess of thiol compound is added to an isocyanate compound. For example, 5 g of one or thiol compounds can be added to 1.8 g of one or more isocyanate compounds in a two neck round bottom flask at room temperature. The flask can be purged with $N_2$ gas for one hour. A catalytic amount of triethyl amine is added. The flask is again purged with $N_2$ gas for 10 minutes and immersed in an ice bath for four hours. A second mid-IR spectrum can be taken at this point. The isocyanate peak at 2270 cm$^{-1}$ will be reduced (potentially to zero) if the reaction is complete. The resulting mixture is added drop wise to a volume of hexane that is 4× the volume of the mixture. This is allowed to separate at least 4 hours. The supernatant is discarded and the product is resuspended in dry acetone. Solvent is removed with rotary evaporation.

In a second example, an isocyanate-terminated thiourethane oligomer can be produced when an excess of isocyanate compound is added to a thiol compound. For example, 5 g of one or more isocyanate compounds can be added to 2 g of one or more thiol compounds in a two neck round bottom flask at room temperature. A mid-IR spectrum can be taken at this point. The flask is purged with $N_2$ gas for one hour. A catalytic amount of triethyl amine is added. The flask is again purged with $N_2$ gas for 10 minutes and immersed in an ice bath for four hours. A second mid-IR spectrum can be taken at this point. The thiol peak can be reduced (potentially to zero) if the reaction is complete. The resulting mixture is added drop wise to a volume of hexane that is 4× the volume of the mixture. This is allowed to separate at least 4 hours. The supernatant is discarded and the product is resuspended in dry acetone. Solvent is removed with rotary evaporation.

Dental composites comprising the disclosed compounds are also contemplated. Such dental composites can comprise the methacrylate/thiourethane oligomer compositions described. Such dental composites can further comprise tertiary amine, d-camphorquinone, inhibitors, and other compositions, including one or more filler compositions In such composites, a thiourethane oligomer can comprise at least 10% of the total weight of the dental composite.

EXAMPLES

Example 1

Screening of Methacrylamide Monomers

Materials were made polymerizable by the addition of camphorquinone (0.5% by weight), ethyl-4-ethylaminoethyl benzoate (0.8% by weight) and 2-phenyliodonium hexafluorophosphate (0.5% by weight). Materials (n=3) were exposed for 10 min at 800 mW/cm² using a mercury arc lamp filtered to 320-500 nm.

Figure 1:
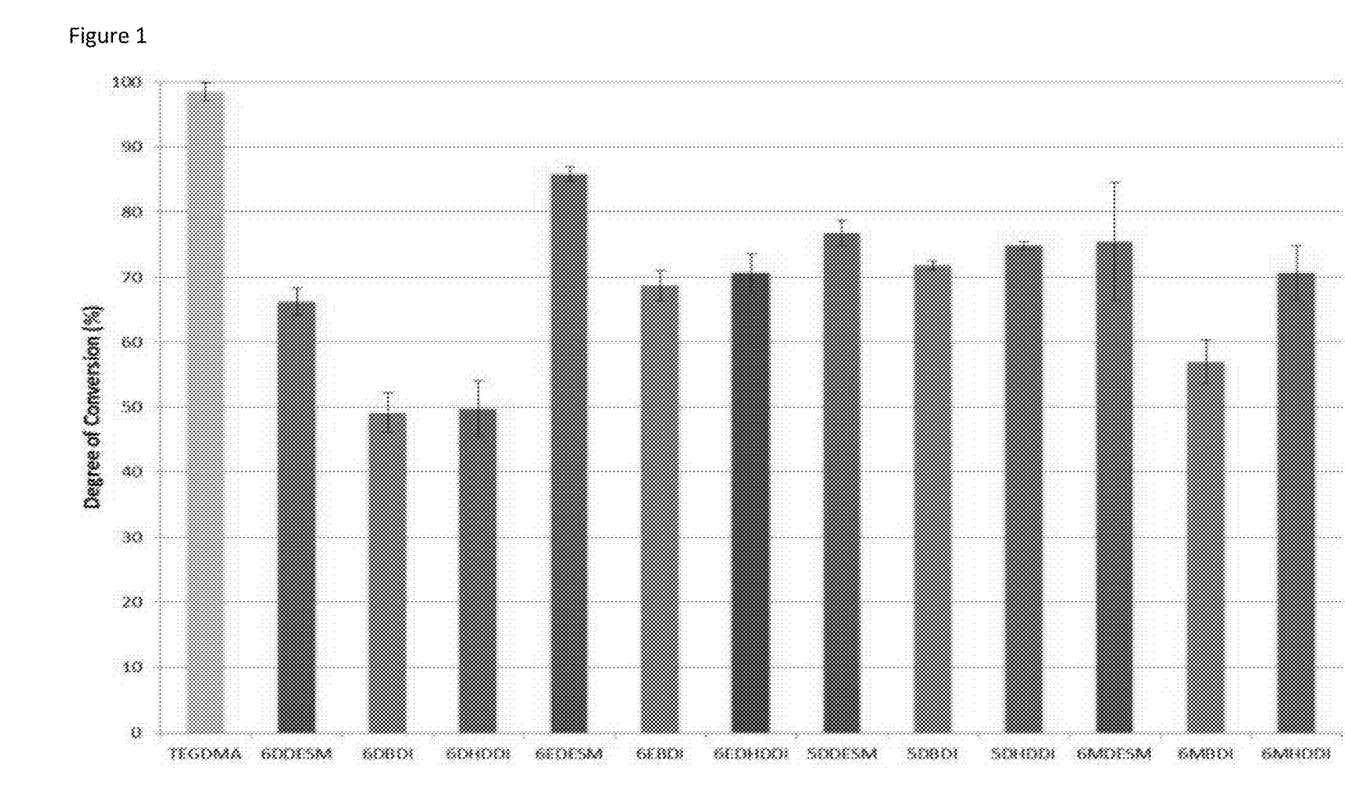
FIG. 1 depicts the degree of conversion measured in mid-IR for the indicated methacrylamides as well as TEGDMA. All were formulated with 0.5% by weight CQ, 0.8% by weight EDMAB, and 0.5% by weight DPI-PF6 and polymerized at 800 mW/cm² for 10 minutes.

The degree of vinyl conversion was followed in mid-infrared using the fundamental band at 3095 cm⁻¹. This band was used instead of the more common 1640 cm⁻¹ due to peak overlap and baseline issues. The band at 1720 cm⁻¹ corresponding to the carbonyl bond was used as an internal reference. The results for this test are shown in FIG. 4. All materials reached conversion values greater than 50%, with some examples reaching conversion as high as 85%. The rates of polymerization, however, are significantly lower than the methacrylate control (by 2-3 fold).

Figure 2:
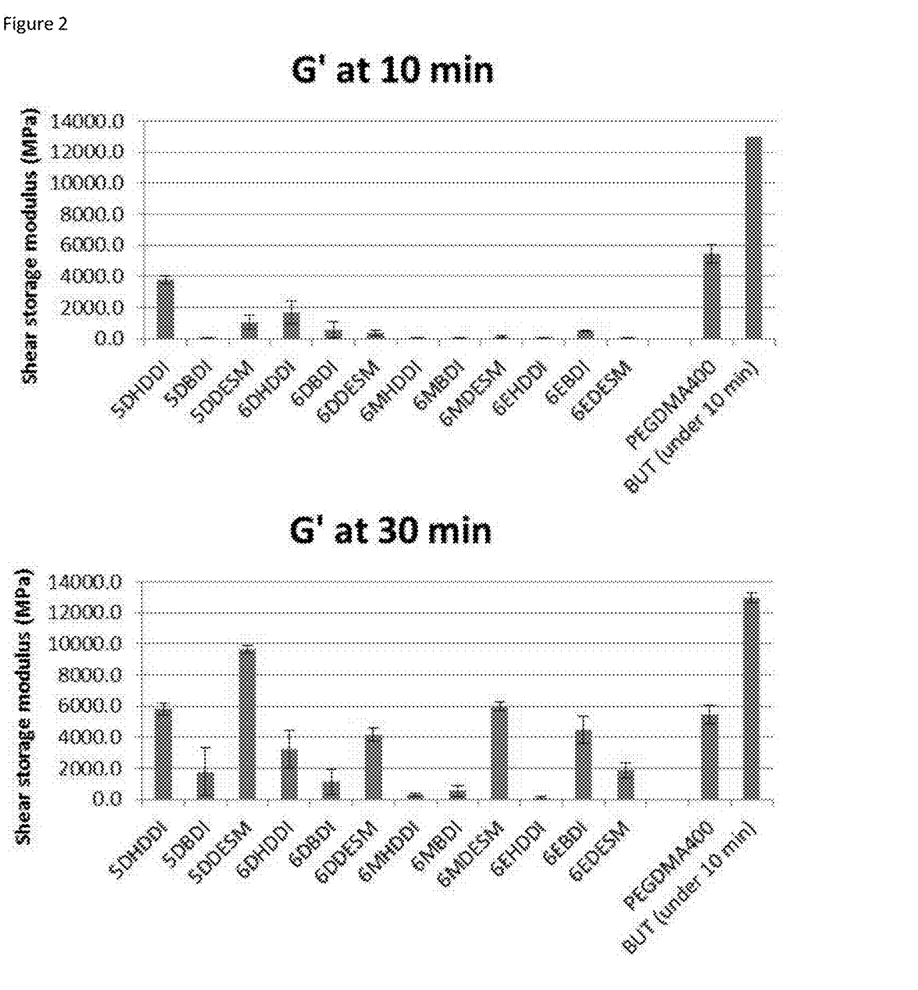
FIG. 2 depicts the shear storage modulus (G') measured in a parallel plate rheometer for the indicated methacrylamides, PEGDMA and a mixture of BisGMA/UDMA/TEGDMA at 5/3/2. All were formulated with 0.5% by weight CQ, 0.8% by weight EDMAB, and 0.5% by weight DPI-PF6 and polymerized at 800 mW/cm² for 10 minutes.

The methacrylate monomers were produced in small quantities, not enough to produce the required amount of flexure bars. Therefore, shear modulus was measured using a DHR-1 rheometer (TA Instruments) using a 20 µm gap, at a frequency of 1 Hz and strain of 0.1%. The rheometer is equipped with a UV-accessory that allows for light access and in situ curing. The light intensity actually reaching the specimen was the same as used for the IR experiments. Total exposure time was 30 min, with data being collected every 1 s. Results for shear modulus at 10 and 30 min are shown in FIG. 5.

Polyethylene glycol dimethacrylate (PEGDMA) was used as the control because its mechanical properties allowed the shear modulus of all materials to be collected using the same parameters on the rheometer. Storage shear modulus (G') was lower for all methacrylamides compared to a dimethacrylate control (PEGDMA) at 10 min. At 30 min, some methacrylamides presented similar or greater G' than the control, adding evidence for the slower polymerization rate and network formation of the current systems.

Example 2

Additional Compounds Synthesized

-continued

6MHDDI

6DBDI

6DHMDI

6DHMDI

6DBDI

6EHMDI

6EHDDI

The invention claimed is:

1. A compound with the structure:

wherein X is a 5- or 6-membered heterocycloalkyl, wherein n is an integer selected from 0, 1, and 2, and wherein R is selected from alkyl, substituted alkyl, aryl, substituted aryl, or dicycloalkyl.

2. The compound of claim 1 wherein X is a 5-membered ring and n=0.

3. The compound of claim 2 wherein R is selected from:

4. The compound of claim 1 wherein X is a 6-membered ring.

5. The compound of claim 4 wherein n=0.

6. The compound of claim 5 wherein R is selected from

7. The compound of claim 4 wherein n=1.

8. The compound of claim 7 wherein R is selected from

9. The compound of claim 4 wherein n=2.

10. The compound of claim 9 wherein R is selected from

11. The compound of claim 3 selected from the group of:

12. The compound of claim 6 selected from the group of:

13. The compound of claim 8 selected from the group of:

14. The compound of claim 10 selected from the group of:

* * * * *

UNITED STATES PATENT AND TRADEMARK OFFICE
CERTIFICATE OF CORRECTION

PATENT NO. : 10,342,745 B2
APPLICATION NO. : 15/154699
DATED : July 9, 2019
INVENTOR(S) : Carmem S. Pfeifer, Jack L. Ferracane and Wilbes Mbiya It is certified that error appears in the above-identified patent and that said Letters Patent is hereby corrected as shown below:

In the Specification

Column 1, Lines 6 to 10, within the ACKNOWLEDGEMENT OF GOVERNMENT SUPPORT, replace:
"This invention was made with the support of the United States government under the terms of grant number U01 DE02756, awarded by the National Institutes of Health. The United States government has certain rights to this invention."
With the following:
--This invention was made with government support under DE023756 awarded by the National Institutes of Health. The government has certain rights in the invention.--

Signed and Sealed this
Twenty-first Day of March, 2023

Katherine Kelly Vidal
Director of the United States Patent and Trademark Office